United States Patent

Namekawa et al.

Patent Number: 5,296,616
Date of Patent: Mar. 22, 1994

[54] OPTICALLY ACTIVE FLUORINE-CONTAINING COMPOUND

[75] Inventors: Masaaki Namekawa; Shinichi Nayuki; Keizou Itoh; Mitsunori Takeda; Yoshinobu Murayama, all of Ibaraki, Japan

[73] Assignee: Kashima Oil Company, Tokyo, Japan

[21] Appl. No.: 989,541

[22] Filed: Dec. 11, 1992

[30] Foreign Application Priority Data

Dec. 26, 1991 [JP] Japan .................. 3-344802

[51] Int. Cl.$^5$ .......................... C07D 309/10
[52] U.S. Cl. ............................ 549/417
[58] Field of Search ................... 549/417

Primary Examiner—Nicky Chan
Attorney, Agent, or Firm—Oblon, Spivak, McClelland, Maier & Neustadt

[57] ABSTRACT

There is disclosed an optically active fluorine-containing compound represented by the general formula (I)

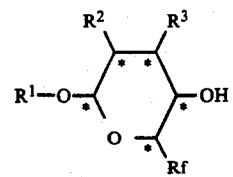

wherein Rf is a fluoroalkyl group having 1 or 2 carbon atoms; $R^1$, $R^2$ and $R^3$, independently of one another, are each a hydrogen atom, a straight or branched chain alkyl group having 1 to 15 carbon atoms, an alkenyl group having 2 to 15 carbon atoms or an aralkyl group having 7 to 10 carbon atoms; and * is an asymmetric carbon atom. The above compound has a fluoroalkyl group with a remarkable electron-attracting property at the asymmetric carbon atom in the tetrahydropyran ring. It is exemplified by tetrahydro-6-trifluoromethyl-2-hexyloxy-4-methyl-5-hydroxypyran and expected to find a wide variety of useful applications as raw materials for an enzyme inhibitor, a bioactive substance, a carcinostatic, a ferroelectric liquid crystal, etc.

10 Claims, No Drawings

OPTICALLY ACTIVE FLUORINE-CONTAINING COMPOUND

BACKGROUND OF THE INVENTION

1. Field of the Invention

The present invention relates to an optically active fluorine-containing compound. More particulary, it pertains to an optically active fluorine-containing compound useful as raw materials for various chemical agents, industrial chemicals, ferroelectric liquid crystals and the like.

2. Description of the Related Arts

As there has been a steady rise in the utilization of liquid crystals in recent years, the development of a liquid crystal having novel structure has been desired.

The research group of the present inventors has hitherto succeeded in the development of a variety of optically active fluorine-containing compounds that are utilizable as the liquid crystals (refer to Japanese Patent Application Laid-Open Nos. 83074/1989, 163143/1989, 233243/1989, 233244/1989, 49743/1990, 167252/1990, 232208/1990, 232209/1990, etc.).

Under such circumstances, intensive research was concentrated by the present inventors on the purpose of developing a novel optically active compound having a tetrahydropyran ring which is of great promise as a new type of liquid crystal.

As a result, it has been found by the present inventors that the aforesaid purpose is attained with a novel compound having a fluoroalkyl group with a remarkable electron-attracting property in itself at the asymmetric carbon atom in a tetrahydropyran ring. The present invention has been accomplished on the basis of the above-mentioned finding and information.

SUMMARY OF THE INVENTION

The present invention provides an optically active fluorine-containing compound represented by the general formula (I)

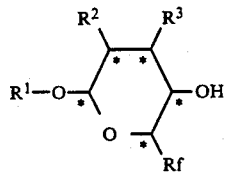

wherein Rf is a fluoroalkyl group having 1 or 2 carbon atoms; $R^1$, $R^2$ and $R^3$ are each independently a hydrogen atom, a straight or branched chain alkyl group having 1 to 15 carbon atoms, an alkenyl group having 2 to 15 carbon atoms or an aralkyl group having 7 to 10 carbon atoms; and * is an asymmetric carbon atom.

DESCRIPTION OF PREFERRED EMBODIMENTS

As mentioned hereinbefore, in the general formula (I) Rf stands for a fluoroalkyl group having 1 or 2 carbon atoms and specifically exemplified by a trifluoromethyl group, a difluoromethyl group, a chlorodifluoromethyl group and a pentafluoroethyl group, of which is preferable a trifluoromethyl group.

$R^1$, $R^2$ and $R^3$, independently of one another, are each a hydrogen atom; a straight or branched chain alkyl group having 1 to 15 carbon atoms, an alkenyl group having 2 to 15 carbon atoms or an aralkyl group having 7 to 10 carbon atoms. Examples of the straight or branched chain alkyl group having 1 to 15 carbon atoms include methyl, ethyl, n-propyl, isopropyl, n-butyl, sec-butyl, tert-butyl, n-pentyl, isopentyl, 1-methylbutyl, n-hexyl, n-heptyl, 1-methylheptyl, n-octyl, 1-ethylheptyl, 1-methyloctyl, n-nonyl, 1-ethyloctyl, 1-methylnonyl, n-decyl, n-undecyl, n-dodecyl, n-tridecyl, n-tetradecyl and n-pentadecyl groups.

Examples of the alkenyl group having 2 to 15 carbon atoms include vinyl, allyl, 1-propenyl, isopropenyl, 1-butenyl, 2-butenyl, 2-methylallyl, 1-pentenyl, 1-hexenyl, 1-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl and 2-pentadecenyl groups.

Examples of the aralkyl group having 7 to 10 carbon atoms include benzyl, phenetyl, phenylpropyl and phenylbutyl groups.

The compound of the general formula (I) according to the present invention can be produced by any of the various processes that are exemplified by the following steps: (1) In the case of $RF=CF_3$ and $R^2=R^3=$hydrogen:

Reaction A

Furan is silylated into the compound represented by the general formula (II).

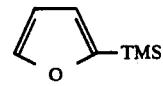

wherein TMS denotes a trimethylsilyl group, and the compound thus produced is trifluoroacetylated into the compound represented by the general formula (III).

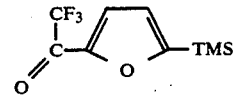

The above-mentioned reaction can be carried out at a temperature of $-78°$ to $0°$ C. by silylating furan using an organolithium compound such as n-butyllithium and trimethylsilyl chloride in a solvent such as tetrahydrofuran and diethyl ether and thereafter trifluoroacetylating the reaction product by the use of the aforementioned n-butyllithium and ethyl trifluoroacetate.

Reaction B

The compound represented by the general formula (III) thus produced is reduced into the compound represented by the general formula (IV)

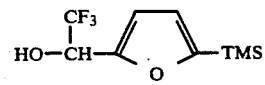

wherein TMS is as defined above. The above-mentioned reaction can be put into practice by using, for example, sodium borohydride, lithium aluminum hydride and stannic chloride.

The obtained compound represented by the general formula (IV) is acylated by reacting it with an acid chloride. Specific examples of the acid chloride usable as an acylating agent include acetyl chloride, propionyl chloride, isobutyloyl chloride, octanoyl chloride and benzoyl chloride.

Reaction C

The obtained compound represented by the general formula (V)

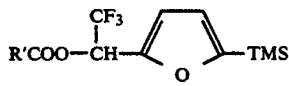

wherein R'CO denotes an acyl group, is subjected to asymmetric hydrolysis by the use of an enzyme to produce an optically active alcohol represented by the general formula (VI)

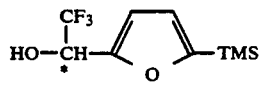

wherein TMS and * are as defined above and an optically active ester represented by the general formula (VIa)

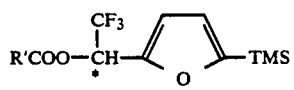

wherein R'CO, TMS and * are as defined above. As the enzyme to be used in the aforesaid reaction, there may be used a variety of enzymes insofar as they are each a so called hydrolysis enzyme, which are exemplified by lipase PS, lipase MY, lipase OF and cellulase. The ester represented by the general formula (VIa) is convertible to an optically active alcohol having a mirror image relation with the alcohol represented by the general formula (VI) by means of chemical hydrolysis or asymmetric hydrolysis with another enzyme.

Reaction D

The alcohol represented by the general formula (VI) thus obtained is silylated to produce the compound represented by the general formula (VII)

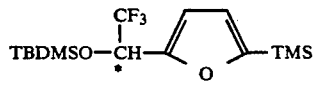

wherein TBDMS designates tert-butyldimethylsilyl group, and TMS and * are as defined above. The reaction can be conducted by the use of tert-butyldimethylsilyl chloride as a silylating agent.

Reaction E

The silylated derivative represented by the general formula (VII) thus obtained is oxidized to afford the compound represented by the general formula (VIII)

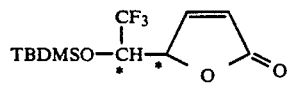

wherein TBDMS and * are as defined above. The aforesaid reaction can be carried out by the use of an oxidizing agent such as monoperoxyphthalic acid-magnesium salt and hydrogen peroxide in the presence of a solvent such as acetic acid and chloroform. In the above reaction, a mixture of diastereomers is also produced but can be easily separated from each other by means of silica-gel column chromatography.

Reaction F

The compound represented by the general formula (VIII) thus obtained is hydrogenated by the conventional method to afford the compound represented by the general formula (IX)

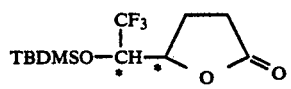

wherein TBDMS and * are as defined above. The hydrogenation can be performed in a solvent such as ethanol, methanol, hexane, ethyl acetate, benzene and toluene by the use of palladium charcoal in an atmosphere of hydrogen.

Reaction G

The lactone derivative represented by the general formula (IX) thus obtained is reduced to afford the compound represented by the general formula (X)

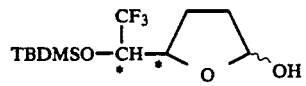

wherein TBDMS and * are as defined above. The reaction can be accomplished by the use of, for example, diisobutylaluminum hydride as the reducing agent at a temperature of $-20°$ C. to $-78°$ C. in a solvent such as diethyl ether and tetrahydrofuran.

Reaction H

The γ-lactol represented by the general formula (X) thus obtained is treated with a base to afford the compound represented by the general formula (XI)

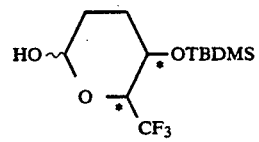

wherein TBDMS and * are as defined above. The reaction can be carried out by the use of potassium tert-butoxide as the base at a temperature of $-20°$ C. to $-78°$ C. in a solvent such as diethyl ether and tetrahydrofuran.

Reaction I

The δ-lactol represented by the general formula (XI) thus obtained is reacted with the alcohol represented by the general formula $R^1OH$ wherein $R^1$ is as defined above to afford the compound represented by the general formula (XII)

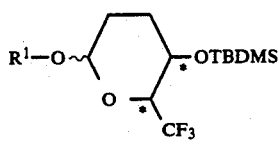

wherein $R^1$, TBDMS and * are as defined above. The reaction can be conducted by the use of an acid catalyst such as p-toluenesulfonic acid at a temperature of 0° to 50° C. in an alcohol as the solvent.

Reaction J

The compound represented by the general formula (XII) thus obtained is subjected to desilylation to afford the objective optically active fluorine-containing compound represented by the general formula (XIII)

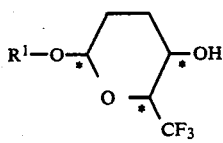

wherein $R^1$ and * are as defined above. The desilylation reaction can be put into practice by the use of tetra-n-butylammonium fluoride as the catalyst at a temperature of 0° to 50° C. in a solvent such as tetrahydrofuran. The two types of diastereomers that are formed in the reaction producing the compound represented by the general formula (X) can be easily separated from the objective compound in the reaction J by means of silica-gel column chromatography.

(2) In the case of $RF=CF_3$, $R^3$=hydrogen:

The compound represented by the general formula (IX) obtained by the above-mentioned reaction F in the preceding item (1) is reacted with an alkyl halide, an aralkyl halide, an alkenyl halide or the like each represented by the general formula $R^2X$ wherein $R^2$ is as defined above and X stands for a halogen to afford the compound represented by the general formula (XIV)

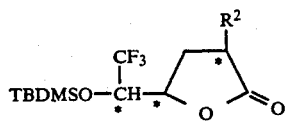

wherein $R^2$, TBDMS and * are as defined above. The reaction can be carried out at −78° C. by the use of n-butyllithium and an organic base such as hexamethyldisilazane and diisopropylamine in a solvent such as tetrahydrofuran and an ether.

Subsequently the compound represented by the general formula (XIV) thus obtained is incorporated in the above reactions G to J of the preceding item (1) to afford the objective optically active fluorine-containing compound represented by the general formula (XV)

wherein $R^1$, $R^2$ and * are as defined above.

(3) In the case of $RF=CF_3$, $R^2$=hydrogen:

The compound represented by the general formula (VIII) obtained by the above-mentioned reaction E in the preceding item (1) is reacted with an alkyl halide, an aralkyl halide, an alkenyl halide or the like each represented by the general formula $R^3X$ wherein $R^3$ is as defined above and X stands for a halogen to afford the compound represented by the general formula (XVI)

wherein $R^3$, TBDMS and * are as defined above. The reaction can be conducted at −78° C. by the use of an organocopper reagent such as di-n-butylcopper lithium. In the above reaction, a mixture of diastereomers is not obtained but only anti-form compounds are produced.

Subsequently the compound represented by the general formula (XVI) thus obtained is incorporated in the above-mentioned reactions G to J of the preceding item (1) to afford the objective optically active fluorine-containing compound represented by the general formula (XVII)

wherein $R^1$, $R^3$ and * are as defined above.

Typical examples of the compounds represented by the general formula (I) according to the present invention include

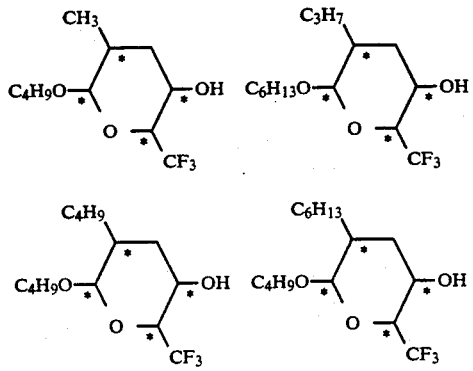

-continued
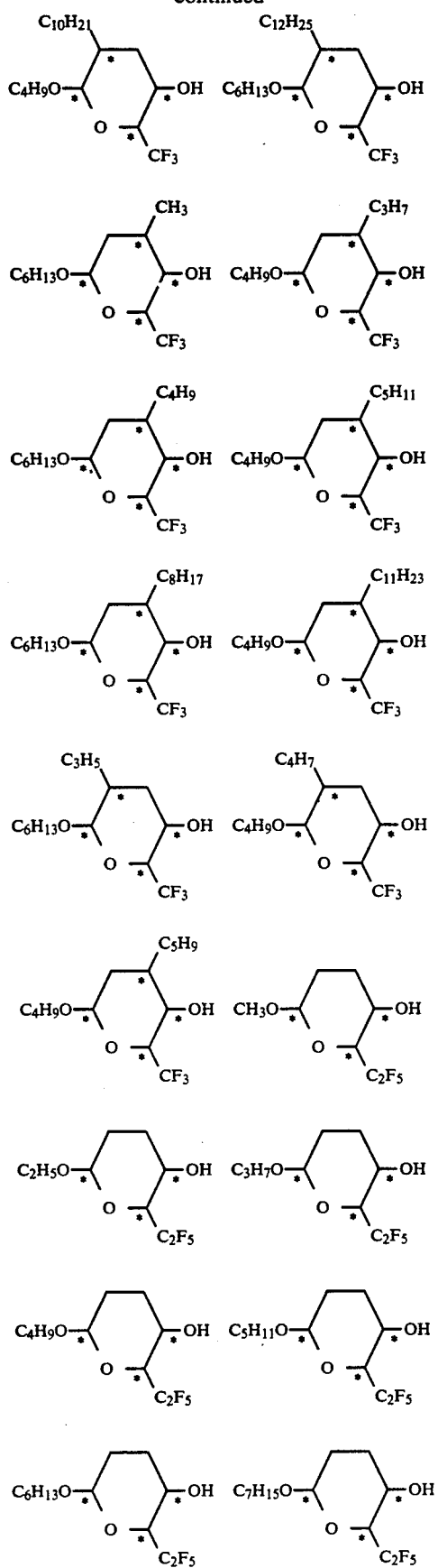
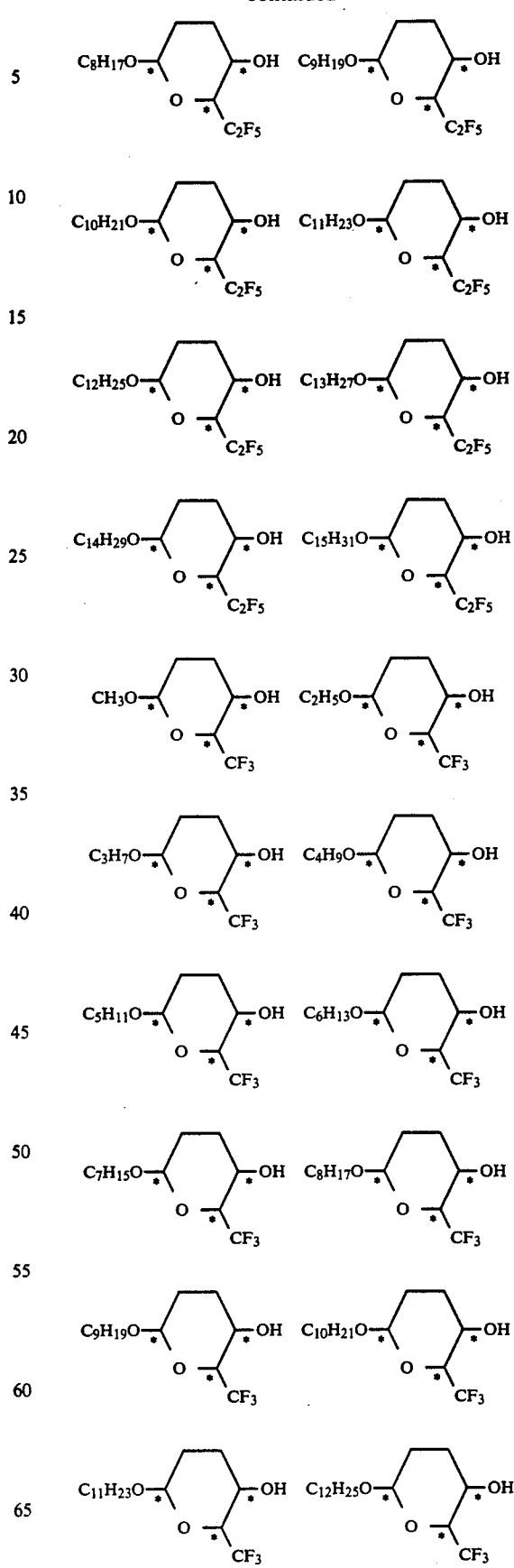

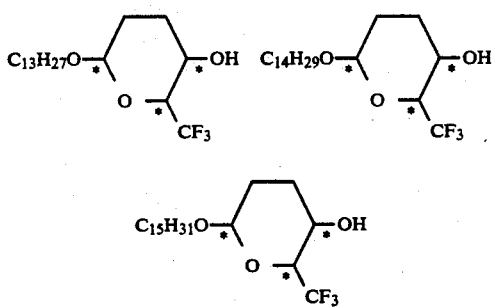

According to the present invention, there is obtained a novel compound having a fluoroalkyl group with a remarkable electron-attracting property in itself at the asymmetric carbon atom in the tetrahydropyran ring. Accordingly, the optically active fluorine-containing compound of the present invention is expected to find a wide variety of applications as raw materials for an enzyme inhibitor, a bioactive substance, a carcinostatic, a ferroelectric liquid crystal and the like.

In the following, the present invention will be described in more detail with reference to the examples, but the present invention is not limited thereto. In each of the examples, the representations of R and S for the optically active compound represented by the general formula (I) are based on the position numbers in the following formula:

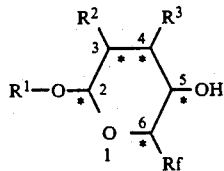

EXAMPLE 1

Synthesis of (2R, 5S, 6S)-tetrahydro-6-trifluoromethyl-2-hexyloxy-5-hydroxypyran and (2S, 5S, 6S)-tetrahydro-6-trifluoromethyl-2-hexyloxy-5-hydroxypyran

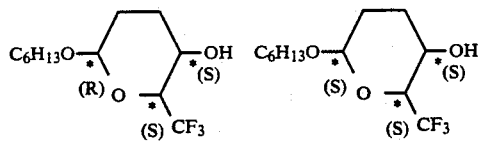

(a) In an atmosphere of nitrogen, 13.6 g (200 mmol) of furan was added to 150 ml of tetrahydrofuran, and 133 ml (200 mmol) of a solution of n-butyllithium in hexane in a concentration of 1.5 mol/liter at −20° C. was added dropwise to the above mixture to proceed with reaction for one hour. Then 21.7 g (200 mmol) of trimethylsilyl chloride was added dropwise to the mixture with stirring at −20 C for one hour. Subsequently 133 ml (200 mmol) of a solution of n-butyllithium in hexane in a concentration of 1.5 mol/liter was added to the mixture to proceed with reaction at −20° C. for one hour and thereafter 28.4 g (200 mmol) of ethyl trifluoroacetate at −78° C. was added dropwise to the resultant mixture to proceed with reaction at −78° C. for one hour and at room temperature for further one hour. The reaction solution was incorporated with 3N hydrochloric acid to arrest the reaction, and the reaction product was extracted with ethyl acetate. Then the extract was washed with successive, saturated solution of sodium hydrogencarbonate and brine and was dried with magnesium sulfate anhydride. The ethyl acetate was vacuum distilled away to give a crude furan-derivative product.

(b) Sodium borohydride in an amount of 2.3 g (60 mmol) was added to 100 ml of dry ethanol, and the crude furan-derivative product as obtained by the above-mentioned reaction was added dropwise to the above ethanol solution at 0° C. over a period of 30 minutes to proceed with reaction at room temperature for 2 hours. Thereafter the ethanol was vacuum distilled away, 3N hydrochloric acid was added to the reaction product to arrest the reaction, and the reaction product was washed with successive, saturated solution of sodium hydrogencarbonate and brine and dried with magnesium sulfate anhydride. The ethyl acetate was vacuum distilled away, and the residue was subjected to vacuum distillation to afford 40.5 g (170 mmol) of an alcoholic compound.

(c) Methylene chloride in an amount of 200 ml was incorporated with 23.8 g (100 mmol) of the alcoholic compound as obtained by the reaction in the preceding (b) and 8.9 ml (110 mmol) of pyridine. Then 8.6 g (110 mmol) of acetyl chloride at 0° C. was added dropwise to the above mixture to proceed with reaction at room temperature for 12 hours. Subsequently 3N hydrochloric acid was added to the reaction product to arrest the reaction, and the reaction product was extracted with methylene chloride. Thereafter the extract was washed with successive, saturated solution of sodium hydrogencarbonate and distilled water and was dried with magnesium sulfate anhydride. The methylene chloride was vacuum distilled away, and the residue was subjected to vacuum distillation to provide 27.5 g (98 mmol) of an esterified compound.

(d) To 1000 ml of distilled water was added 28.0 g (100 mmol) of the esterified compound as obtained by the above-mentioned reaction, and the resultant mixture was stirred at 40° C. in a mini-jar type fermenter. Then 20 g of lipase PS was added thereto to proceed with reaction for 20 hours, which was stopped by the addition of 3N hydrochloric acid and cooling to 0° C. The reaction product was filtered with Celite, the product in the filtrate was extracted with ethyl acetate, washed with brine and dried with magnesium sulfate anhydride, and the ethyl acetate was vacuum distilled away. Subsequently, the resultant reaction product was purified by separation by means of silica-gel column chromatography to give 11.7 g (49 mmol) of an optically active alcoholic compound and 13.2 g (47 mmol) of an optically active esterified compound. The alcoholic compound thus obtained had an optical purity of 97.5% e.e.

(e) In 100 ml of methylene chloride was dissolved 11.7 g (49 mmol) of the optically active alcoholic compound obtained by the above-mentioned reaction and to the resultant solution were added 4.0 g (59 mmol) of imidazole and 8.9 g (59 mmol) of tert-butyldimethylsilyl chloride at 0° C. with stirring for 15 minutes to proceed with reaction at room temperature for 16 hours. The reaction was stopped by the addition of distilled water. The reaction product was extracted with methylene chloride, then washed with distilled water and dried with magnesium sulfate anhydride. After the methylene chloride was vacuum distilled away, the resultant reaction product was purified by separation by means of column chromatography to afford 16.6 g (47 mmol) of a silyl ether compound.

(f) In an atmosphere of nitrogen, to 120 ml of acetic acid were added 14.1 g (40 mmol) of the silyl ether compound as obtained by the above-mentioned reaction and 23.2 g (60 mmol) of magnesium monoperoxyphthalate to proceed with reaction at 80° C. for 12 hours. After the acetic acid was vacuum distilled away, a saturated solution of sodium hydrogencarbonate was added to the reaction product, which was extracted with ethyl acetate. Then the extract was washed with brine and dried with magnesium sulfate anhydride. After the ethyl acetate was vacuum distilled away, the resultant reaction product was purified by separation by means of column chromatography to provide 4.7 g (16 mmol) of (4S, 1'S) butenolide compound and 3.0 g (10 mmol) of (4R, 1'S) butenolide compound. In addition, the raw material in an amount of 4.2 g (12 mmol) was recovered.

(g) In 40 ml of ethanol was dissolved 13.7 g (46 mmol) of the mixture of (4S, 1'S)-and (4R, 1'S)-butenolide compound as obtained by the above-mentioned reaction without separation from each other. To the resultant solution was added 1.4 g of 10% Pd/C (containing 10% by weight of Pd) to proceed with reaction in an atmosphere of hydrogen at room temperature for 15 hours. After the resultant reaction solution was filtered and the solvent (ethanol) was vacuum distilled away, the resultant reaction product was purified by separation by means of silica-gel column chromatography to give 8.2 g (29 mmol) of (4S, 1'S)butanolide compound and 3.6 g (12 mmol) of (4R, 1'S)butanolide compound.

(h) In an atmosphere of nitrogen, to 40 ml of diethyl ether was added 7.5 g (25 mmol) of the (4S, 1'S)butanolide compound as obtained by the above-mentioned reaction and added dropwise 32 ml (30 mmol) of a solution of diisobutylaluminum hydride in n-hexane in 0.93 mol/liter concentration at −78° C. to proceed with reaction for 3 hours. The reaction was stopped by the addition of distilled water, and the resultant reaction product was neutralized with 1N hydrochloric acid and extracted with diethyl ether. Then the extract was washed with brine, and dried with magnesium sulfate anhydride, and the diethyl ether was vacuum distilled away. Subsequently the resultant reaction product was purified by separation by means of silica-gel column chromatography to provide 7.3 g (24 mmol) of a lactol compound.

(i) In an atmosphere of nitrogen, to 50 ml of tetrahydrofuran was added 7.3 g (24 mmol) of the lactol compound as obtained by the aforestated reaction and added dropwise a solution of 3.0 g (27 mmol) of potassium tert-butoxide in 10 ml of tetrahydrofuran at −78° C. to proceed with reaction for 3 hours. The reaction was stopped by the addition of distilled water, and the resultant reaction product was neutralized with 1N hydrochloric acid and extracted with diethyl ether. Then the extract was washed with brine, and dried with magnesium sulfate anhydride, and the diethyl ether was vacuum distilled away. Subsequently the resultant reaction product was purified by separation by means of silica-gel column chromatography to afford 6.4 g (21 mmol) of a pyranose compound.

(j) In 40 ml of hexane was dissolved 6.4 g (21 mmol) of the pyranose compound as obtained by the above-mentioned reaction. To the solution thus formed was added 0.1 g of p-toluenesulfonic acid to proceed with reaction at room temperature for 18 hours. The reaction solution as such was purified by separation by means of silica-gel column chromatography to give 8.0 g (21 mmol) of an acetal compound. The compound thus obtained was a mixture of diastereomers, which was used in the following reaction without being separated from each other.

(k) In 20 ml of tetrahydrofuran was dissolved 8.0 g (21 mmol) of the acetal compound as obtained by the aforementioned reaction. To the resultant solution was added 10 ml of a solution of tetra-n-butylammonium fluoride in tetrahydrofuran in 1.0 mol/liter concentration to proceed with reaction at 0° C. for one hour and at room temperature for further 40 hours. The reaction was stopped by the addition of distilled water, and the reaction product was extracted with diethyl ether. Then the extract was washed with brine and dried with magnesium sulfate anhydride. After the diethyl ether was vacuum distilled away, the resultant reaction product was purified by separation by means of silica-gel column chromatography to give the objective compounds comprising 3.0 g (11 mmol) of (2R, 5S, 6S)-tetrahydro-6-trifluoromethyl-2-hexyloxy-5-hydroxypyran and 2.3 g (8 mmol) of (2S, 5S, 6S)-tetrahydro-6-trifulromethyl-2-hexyloxy-5-hydroxypyran.

The physical properties of the compounds obtained in the aforestated procedures are give hereunder.

(1) (2R, 5S, 6S)-compound
Molecular formula: $C_{12}H_{21}F_3O_3$
$^1$H-NMR (nuclear magnetic resonance method with proton);

| δ (ppm) | |
| --- | --- |
| 0.88 | (t, J=6.5Hz, 3H) |
| 1.20 to 1.39 | (m, 6H) |
| 1.50 to 1.71 | (m, 4H) |
| 1.83 to 2.04 | (m, 2H) |
| 2.13 to 2.22 | (m, 1H) |
| 3.46 | (dt, J=9.4, 6.9Hz, 1H) |
| 3.66 | (dq, J=8.9, 6.3Hz, 1H) |
| 3.81 to 3.93 | (m, 2H) |
| 4.52 | (dd, J=2.0, 8.7Hz, 1H) |

$^{19}$F-NMR (nuclear magnetic resonance method with fluorine isotope, reference: $CFCl_3$); δ (ppm)
−75.13   (d, J=6.3Hz)

IR (infrared absorption: $cm^{-1}$) 3450, 1275, 1170, 1145, 1090, 940

Mass spectrometric analysis m/e ($M^+ +H$)

| Calculated | 271.1521 |
| --- | --- |
| Found | 271.1512 |

$[α]_D^{25} = −36.0°$ (C (concentration) = 1.05, solvent:methanol)

(2) (2S, 5S, 6S)-compound
Molecular formula: $C_{12}H_{21}F_3O_3$
$^1$H-NMR; δ (ppm)

| 0.90 | (t, J=7.3Hz, 3H) |
| --- | --- |
| 1.23 to 1.45 (m, 6H) | |
| 1.52 to 1.67 (m, 2H) | |
| 1.76 to 2.00 (m, 5H) | |
| 3.42 | (dt, J=9.7, 6.4Hz, 1H) |
| 3.68 | (dt, J=9.7, 6.8Hz, 1H) |
| 3.79 to 3.98 (m, 2H) | |
| 4.86 | (m, 1H) |

$^{19}$F-NMR (reference: $CFCl_3$); δ (ppm)
−75.17   (d, J=6.2Hz)

IR ($cm^{-1}$) 3400, 1270, 1175, 1130, 1045, 945

Mass spectrometric analysis m/e ($M^+ +H$)

| Calculated | 271.1521 |
| --- | --- |
| Found | 271.1493 |

$[α]_D^{25} = +86.5°$ (C (concentration) = 1.08, solvent:methanol)

EXAMPLE 2

Synthesis of (2R, 5S, 6S)-tetrahydro-2-butoxy-6-trifluoromethyl-5-hydroxypyran and (2S, 5S, 6S)-tetrahydro-2-butoxy-6-trifluoromethyl-5-hydroxypyran

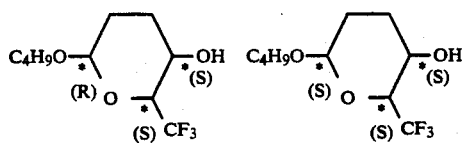 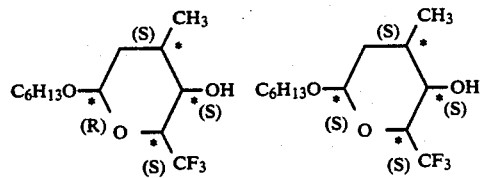

(a) The pyranose compound as obtained in Example 1 (i) in an amount of 1.7 g (5.7 mmol) was dissolved in 15 ml of butanol and the procedure in Example 1 (j) was repeated to afford 1.9 g (5.3 mmol) of an acetal compound, which was a mixture of diastereomers and used for the reaction described hereunder without being separated from one another.

(b) By the use of 1.9 g (5.3 mmol) of the acetal compound as obtained by the above-mentioned reaction, the procedure in Example 1 (k) was repeated to provide the objective compounds comprising 0.64 g (2.6 mmol) of (2R, 5S, 6S)-tetrahydro-2-butoxy-6-trifluoromethyl-5-hydroxypyran and 0.59 g (2.4 mmol) of (2S, 5S, 6S)-tetrahydro-2-butoxy-6-trifluoromethyl-5-hydroxypyran.

The physical properties of the compounds obtained in the above-mentioned procedures are given hereunder.

(1) (2R, 5S, 6S)-compound

Molecular formula: $C_{10}H_{17}F_3O_3$ $^1$H-NMR; δ(ppm)

| 0.92 | (t, J=7.3Hz, 3H) |
|---|---|
| 1.30 to 1.45 | (m, 2H) |
| 1.52 to 1.65 | (m, 4H) |
| 1.88 to 2.22 | (m, 3H) |
| 3.47 | (dt, J=9.5, 6.8Hz, 1H) |
| 3.67 | (dq, J=9.0, 6.2Hz, 1H) |
| 3.79 to 3.96 | (m, 2H) |
| 4.52 | (dd, J=2.0, 8.6Hz, 1H) |

$^{19}$F-NMR (reference: CFCl$_3$); δ (ppm)
    −75.17    (d, J=6.3Hz)

IR (cm$^{-1}$) 3450, 1270, 1170, 1145, 1090, 940

Mass spectrometric analysis m/e (M$^+$+H)

| Calculated | 243.1208 |
|---|---|
| Found | 243.1204 |

$[α]_D^{26}$ = −40.8° (C (concentration) = 1.07, solvent:methanol)

(2) (2S, 5S, 6S)-compound

Molecular formula: $C_{10}H_{17}F_3O_3$ $^1$H-NMR; δ (ppm)

| 0.94 | (t, J=7.3Hz, 3H) |
|---|---|
| 1.32 to 1.47 | (m, 2H) |
| 1.53 to 1.66 | (m, 2H) |
| 1.77 to 2.03 | (m, 5H) |
| 3.43 | (dt, J=9.7, 6.3Hz, 1H) |
| 3.69 | (dt, J=9.7, 6.7Hz, 1H) |
| 3.82 to 3.93 | (m, 2H) |
| 4.86 | (m, 1H) |

$^{19}$F-NMR (reference: CFCl$_3$); δ (ppm)
    −75.20    (d, J=6.2Hz)

IR (cm$^{-1}$) 3400, 1270, 1175, 1135, 1050, 945

Mass spectrometric analysis

| Calculated | 243.1208 |
|---|---|
| Found | 243.1237 |

$[α]_d^{25}$ = +101.8° (C (concentration) = 1.06, solvent:methanol)

EXAMPLE 3

Synthesis of (2S, 4S, 5S, 6S)-tetrahydro-6-trifluoromethyl-2-hexyloxy-4-methyl-5-hydroxypyran and (2R, 4S, 5S, 6S)-tetrahydro-6-trifluoromethyl-2-hexyloxy-4-methyl-5-hydroxypyran (a) In an atmosphere of nitrogen, 1.9 ml (9.3 mmol) of hexamethyldisilazane was added to 10 ml of tetrahydrofuran, and 5.2 ml (8.5 mmol) of a solution of n-butyllithium in hexane in a concentration of 1.6 mol/liter at −78° C. was added dropwise to the above mixture with stirring for 30 minutes. Then a solution of 2.3 g (7.7 mmol) of the (4S, 1'S)butanolide compound as otabained in Example 1 (g) in 10 ml of tetrahydrofuran was added to the resultant mixture to proceed with reaction at −78° C. for one hour. Thereafter 0.5 ml (8.5 mmol) of methyl iodide was added dropwise to the mixture thus formed to proceed with reaction for 30 minutes. The reaction was stopped with 3N hydrochloric acid, and the resultant reaction product was extracted with ethyl acetate. The extract was washed with successive, saturated solution of sodium hydrogencarbonate and brine, and dried with magnesium sulfate anhydride. After the ethyl acetate was vacuum distilled away, the reaction product was purified by separation by means of silica-gel column chromatography to afford 1.7 g (5.5 mmol) of a methylated compound. In the aforesaid reaction only the anti-form compound was identified and the syn-form compound was not identified.

(b) By the use of the methylated compound as obtained by the above-mentioned reaction, the procedures in Example 1 (h) to (k) were repeated to produce the objective compounds comprising 0.12 g (0.4 mmol) of (2S, 4S, 5S, 6S)-tetrahydro-6-trifluoromethyl-2-hexyloxy-4-methyl-5-hydroxypyran and 0.12 g (0.4 mmol) of (2R, 4S, 5S, 6S)-tetrahydro-6-trifluoromethyl-2-hexyloxy-4-methyl-5-hydroxypyran.

The physical properties of the above-obtained compounds are given hereunder.

(1) (2S, 4S, 5S, 6S)-compound

Molecular formula: $C_{13}H_{23}F_3O_3$ $^1$H-NMR; δ(ppm)

| 0.89 | (t, J=6.5Hz, 3H) |
|---|---|
| 1.10 | (d, J=6.9Hz, 3H) |
| 1.20 to 1.45 | (m, 6H) |
| 1.48 to 1.67 | (m, 3H) |
| 1.85 to 2.23 | (m, 3H) |
| 3.42 | (dt, J=9.6, 6.5Hz, 1H) |
| 3.73 | (dt, J=9.6, 6.7Hz, 1H) |
| 3.93 | (dd, J=4.6, 5.7Hz, 1H) |
| 4.07 | (dg, J=6.0, 7.4Hz, 1H) |
| 4.91 | (dd, J=4.7, 4.9Hz, 1H) |

$^{19}$F-NMR (reference: CFCl$_3$) δ (ppm)
    −76.01    (d, J=7.4Hz)

$[α]_D^{27}$ = +83.9° (C (concentration) = 0.76, solvent:methanol)

(2) (2R, 4S, 5S, 6S)-compound

Molecular formula: $C_{13}H_{23}F_3O_3$ $^1$H-NMR; δ (ppm)

| 0.88 | (t, J=6.7Hz, 3H) |
|---|---|
| 0.99 | (d, J=7.1Hz, 3H) |
| 1.22 to 1.41 | (m, 6H) |
| 1.49 to 1.88 | (m, 5H) |
| 2.27 to 2.42 | (m, 1H) |
| 3.41 | (dt, J=9.5, 6.9Hz, 1H) |
| 3.84 | (dt, J=9.5, 5.8Hz, 1H) |
| 3.85 to 4.05 | (m, 2H) |
| 4.80 | (dd, J=3.4, 5.8Hz, 1H) |

$^{19}$F-NMR (reference: CFCl$_3$); δ (ppm)

-continued

| | |
|---|---|
| −74.69 | (d, J=7.4Hz) |

$[\alpha]_D^{28}$ = −51.1° (C (concentration) = 0.74, solvent:methanol)

EXAMPLE 4

Synthesis of (2S, 3R, 5S, 6S)-tetrahydro-6-trifluoromethyl-2-hexyloxy-3-methyl-5-hydroxypyran and (2R, 3R, 5S, 6S)-tetrahydro-6-trifluoromethyl-2-hexyloxy-3-methyl-5-hydroxypyran

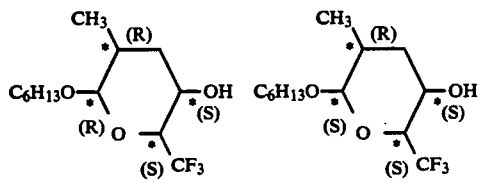

(a) In an atmosphere of nitorgen, 2.7 g (14 mmol) of cuprous iodide was added to 10 ml of tetrahydrofuran, and 28 ml (28 mmol) of a solution of methyllithium in ether in a concentration of 1.0 mol/liter at −78° C. was slowly added dropwise to the above mixture to proceed with reaction at −78° C. for 30 minutes, at room temperature for 5 minutes and further at −78° C. for 30 minutes. Then 3.5 ml (14 mmol) of trifluoroborane-ether complex was added to the mixture with stirring at −78° C. for 30 minutes. Next, a solution of 2.1 g (7.0 mmol) of the (4S, 1′S)butenolide compound as obtained in Example 1 (f) in 5 ml of tetrahydrofuran was added to the mixture to proceed with reaction at −78° C. for 3 hours. The reaction was stopped with dilute aqueous ammonia, and the resultant reaction product was extracted with ethyl acetate. The extract was washed with successive, sodium thiosulfate solution and brine and dried with magnesium sulfate anhydride. The ethyl acetate was vaccum distilled away, and the reaction product was purified by separation by means of silica-gel compound chromatography to give 1.7 g (5.5 mmol) of a methylated compound.

(b) By the use of the methylated compound as obtained by the aforestated reaction, the procedures in Example 1 (h) to (k) were repeated to produce the objective compounds comprising 0.19 g (0.7 mmol) of (2S, 3R, 5S, 6S)-tetrahydro-6-trifluoromethyl-2-hexyloxy-3-methyl-5-hydroxypyran and 0.19 g (0.7 mmol) of (2R, 3R, 5S, 6S)-tetrahydro-6-trifluoromethyl-2-hexyloxy-3-methyl-5-hydroxypyran.

The physical properties of the above-obtained compounds are given hereunder.

(1) (2S, 3R, 5S, 6S)-compound
Molecular formula: $C_{13}H_{23}F_3O_3$
$^1$H-NMR; δ(ppm)

| | |
|---|---|
| 0.90 | (t, J=6.8Hz, 3H) |
| 0.93 | (d, J=6.6Hz, 3H) |
| 1.18 to 1.44 | (m, 6H) |
| 1.52 to 1.71 | (m, 3H) |
| 1.82 to 1.99 | (m, 3H) |
| 3.39 | (dt, J=9.7, 6.5Hz, 1H) |
| 3.70 | (dt, J=9.7, 6.5Hz, 1H) |
| 3.79 to 3.92 | (m, 2H) |
| 4.62 | (d, J=3.0Hz, 1H) |

$^{19}$F-NMR (reference: CFCl$_3$); δ (ppm)

| | |
|---|---|
| −75.10 | (d, J=5.8Hz) |

IR (cm$^{-1}$) 3400, 1270, 1180, 1130
$[\alpha]_d^{25}$ = +97.4° (C (concentration) = 0.79, solvent:methanol)

(2) (2R, 3R, 5S, 6S)-compound
Molecular formula: $C_{13}H_{23}F_3O_3$
$^1$H-NMR; δ (ppm)

| | |
|---|---|
| 0.89 | (t, J=6.7Hz, 3H) |
| 0.96 | (d, J=6.6Hz, 3H) |
| 1.19 to 1.46 | (m, 6H) |
| 1.52 to 1.86 | (m, 3H) |
| 1.90 to 1.99 | (m, 1H) |
| 2.08 to 2.19 | (m, 1H) |
| 3.44 | (dt, J=9.6, 6.8Hz, 1H) |
| 3.63 | (dq, J=9.2, 6.1Hz, 1H) |
| 3.84 to 3.93 | (m, 2H) |
| 4.09 | (d, J=8.4Hz, 1H) |

$^{19}$F-NMR (reference: CFCl$_3$); δ (ppm)

| | |
|---|---|
| −75.10 | (d, J=6.1Hz) |

IR (cm$^{-1}$) 3400, 1275, 1170, 1010
$[\alpha]_D^{27}$ = −47.9° (C (concentration) = 0.74, solvent:methanol)

What is claimed is:

1. An optically active fluorine-containing compound represented by the general formula (I)

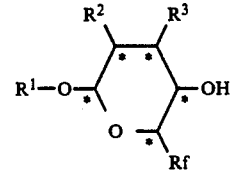

wherein Rf is a fluoroalkyl group having 1 or 2 carbon atoms; R$^1$, R$^2$ and R$^3$, independently of one another, are each a hydrogen atom, a straight or branched chain alkyl group having 1 to 15 carbon atoms, an alkenyl group having 2 to 15 carbon atoms or an aralkyl group having 7 to 10 carbon atoms; and * is an asymmetric carbon atom.

2. The compound according to claim 1 wherein Rf is selected from a trifluoromethyl group, a difluoromethyl group, and a pentafluoroethyl group.

3. The compound according to claim 1 wherein Rf is a trifluoromethyl group.

4. The compound according to claim 1 wherein R$^2$ and R$^3$ are each a hydrogen atom.

5. The compound according to claim 1 wherein R$^2$ is a hydrogen atom.

6. The compound according to claim 1 wherein R$^3$ is a hydrogen atom.

7. The compound according to claim 1 wherein the compound is tetrahydro-6-trifluoromethyl-2-hexyloxy-5-hydroxypyran.

8. The compound according to claim 1 wherein the compound is tetrahydro-2-butoxy-6-trifluoromethyl-5-hydroxypyran.

9. The compound according to claim 1 wherein the compound is tetrahydro-6-trifluoromethyl-2-hexyloxy-4-methyl-5-hydroxypyran.

10. The compound according to claim 1 wherein the compound is tetrahydro-6-trifluoromethyl-2-hexyloxy-3-methyl-5-hydroxypyran.

* * * * *

UNITED STATES PATENT AND TRADEMARK OFFICE
CERTIFICATE OF CORRECTION

PATENT NO. : 5,296,616
DATED : March 22, 1994
INVENTOR(S) : Masaaki Namekawa, et al.

It is certified that error appears in the above-indentified patent and that said Letters Patent is hereby corrected as shown below:

Column 9, line 60, "at -20 C for one hour." should read --at -20°C for one hour.--.

Column 14, line 65, "(dt, J=9.5, 5.8Hz, 1H)" should read --(dt, J=9.5, 6.8Hz, 1H)--.

Signed and Sealed this

Twenty-fifth Day of October, 1994

Attest:

BRUCE LEHMAN

*Attesting Officer*     *Commissioner of Patents and Trademarks*